United States Patent [19]

McPherson et al.

[11] Patent Number: 5,701,913
[45] Date of Patent: Dec. 30, 1997

[54] TISSUE SOFTNESS PROBE

[75] Inventors: Roger W. McPherson; Nigel G. Shrive; Erich Damson; Cyril B. Frank; Fred Lhenen; Norman S. Schachar, all of Calgary, Canada

[73] Assignee: University Technologies International Inc., Calgary, Canada

[21] Appl. No.: 589,263

[22] Filed: Feb. 3, 1995

[51] Int. Cl.⁶ .................................................. A61B 5/103
[52] U.S. Cl. .................................................. 128/774; 128/782
[58] Field of Search .................................. 128/774, 695, 128/645, 692; 73/81, 78, 862.633

[56] References Cited

U.S. PATENT DOCUMENTS

| | | | |
|---|---|---|---|
| 2,366,645 | 1/1945 | Ollendorff | 73/80 |
| 2,708,847 | 5/1955 | Esterman | 73/80 |
| 3,272,001 | 9/1966 | Adise | 73/80 |
| 3,677,074 | 7/1972 | Murr | 73/80 |
| 3,738,355 | 6/1973 | Salvatore | 128/2 |
| 3,831,588 | 8/1974 | Rindner | 128/2.05 |
| 3,945,373 | 3/1976 | Tweed et al. | 128/2 |
| 3,956,924 | 5/1976 | Hansen et al. | 73/81 |
| 4,132,224 | 1/1979 | Randolph | 128/2 |
| 4,159,640 | 7/1979 | Leveque et al. | 73/81 |
| 4,249,417 | 2/1981 | Feldstein et al. | 73/862.633 |
| 4,325,387 | 4/1982 | Helfer | 128/748 |
| 4,364,399 | 12/1982 | Dashefky | 128/774 |
| 5,503,162 | 4/1996 | Athanasiou et al. | 128/774 |

FOREIGN PATENT DOCUMENTS

| | | |
|---|---|---|
| 63-62599 | 3/1988 | Japan. |
| 311620 | 4/1970 | U.S.S.R. |

*Primary Examiner*—Max Hindenburg
*Assistant Examiner*—Pamela L. Wingood
*Attorney, Agent, or Firm*—Anthony R. Lambert

[57] ABSTRACT

A device and method for the measurement of stiffness of cartilage, specifically intended for arthroscopic use. An tissue softness probe is formed from a stiff shaft and flexible shaft, and strain gauges continuously measure the load in the stiff shaft and the deflection of the flexible shaft as they are displaced into cartilage. The stiff shaft and flexible shaft extend away from a probe body beside each other. The stiff shaft is semi-circular in section at one end with a flat side extending along the shaft at that end, and the flexible shaft is a flat shim that is attached to the flat side of the stiff shaft. Such a design advantageously allows the more or less parallel shafts to be inserted into a human body joint for displacement against cartilage, as for example during arthroscopic surgery. The stiff shaft terminates in a plunger extending at right angles to the stiff shaft, with the tip of the plunger lying, in the rest position, between a forked tip of the flexible shaft. In operation, as the plunger tip is displaced into cartilage, the flexible shaft gradually deflects providing a continuous read out from the strain gauge that is indicative of the relative displacement of the plunger tip as it is displaced into the cartilage. Both shafts are mounted to be enclosed within a retractable hollow cannula extending from the probe body.

10 Claims, 2 Drawing Sheets

TISSUE SOFTNESS PROBE

FIELD OF THE INVENTION

This invention relates to apparatus and methods used in the measurement of stiffness of body tissue, particularly cartilage.

BACKGROUND AND SUMMARY OF THE INVENTION

In the presently widely practised method of assessing stiffness, and hence state of health, of cartilage, it is common for a physician to rely upon personal judgment of the stiffness of the cartilage upon manual displacement of the cartilage. Evidently, such a technique is prone to judgment error.

While several techniques have been proposed for the mechanical measurement of hardness of human tissue, no techniques that the inventors are aware of are specifically developed for the particular problem of measuring the stiffness of cartilage.

Thus, in Leveque, U.S. Pat. No. 4,159,640, a device is proposed for the measurement of the hardness of breast tissue. The device includes a support to be applied against the material to be tested and a feeler movably carried by the support for displacement through a distance which will be proportional to the hardness or consistency being measured. In this device, a control circuit is provided for recording the displacement of the feeler only when the bearing pressure of the support on the test material has a predetermined value.

Also, in Randolph, U.S. Pat. No. 4,132,224, there is proposed a durometer for indentible tissue, referred to in Randolph as dental tissue or tissue intended to receive an artificial limb. The durometer is formed from a pair of flat parallel apparently equally flexible steels springs extend forwardly from a handle. One end of one spring beam is forked about an angled indentor end of the other spring beam. Strain gauges on each spring beam measure strain resulting from deflection of the beams. As the indentor deflects sufficiently for the fork ended beam to contact tissue, the signal from the strain gauge on the fork ended beam generates a lock signal that locks the reading of the strain gauge on the indentor.

Thus Randolph and Leveque provide devices that measure a particular value of (a) pressure or (b) displacement when a pre-set value of (a) displacement or (b) pressure is reached respectively. Neither provides continuous measurement of load and displacement.

This invention is particularly intended for the measurement of stiffness of cartilage, and provides a device particularly intended for arthroscopic use and open joint surgery. In addition, the device utilizes a novel method of determining the surface compressive stiffness of cartilage, or other compliant tissue. Tissue is defined herein as any compliant material, whether or not it contains living cells.

In one aspect of the invention, an arthroscopic probe is formed from a stiff shaft and a flexible shaft, and strain gauges continuously measure the strain in each shaft as they are displaced into cartilage. In another aspect of the invention, the stiff shaft and flexible shaft extend away from a probe body beside each other. In a further aspect, the stiff shaft is partially semi-circular in section with a flat side extending along the end portion of the shaft, and the flexible shaft is a flat shim that is attached to the flat side of the stiff shaft. Such a design advantageously allows the more or less parallel shafts to be inserted into a human body joint for displacement against cartilage, as for example during arthroscopic surgery.

It is preferred that the stiff shaft terminates in a plunger extending at right angles to the stiff shaft, with the tip of the plunger lying, in the rest position, between a forked tip of the flexible shaft. In operation, as the plunger tip is displaced into cartilage, the flexible shaft gradually deflects providing a continuous read out from the strain gauge that is indicative of the relative displacement of the plunger tip into the cartilage. The force on the plunger tip is measured with the strain gauge on the stiff shaft.

Both shafts are preferably mounted to be enclosed within a retractable hollow cannula extending from the probe body.

In another aspect of the invention, a load sensing body and a displacement sensing body continuously output an indication of load and displacement respectively while both are pressed adjacent each other into cartilage.

BRIEF DESCRIPTION OF THE DRAWINGS

There will now be described a preferred embodiment of the invention, with reference to the drawings, by way of illustration, in which like numerals denote like elements and in which.

DETAILED DESCRIPTION OF PREFERRED EMBODIMENTS

In this patent document, stiff and flexible indicate relative stiffnesses of one shaft to another. Preferably, stiff in relation to a shaft means that the shaft tends not to bend visibly under a manually applied load, while flexible preferably means that the shaft deflects visibly under a small manually applied load.

Figure 1:
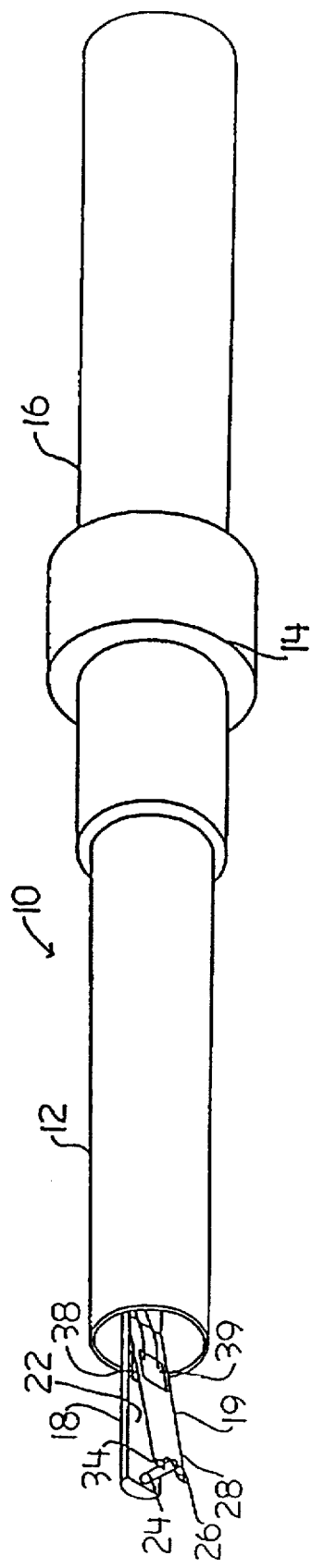
FIG. 1 is a perspective showing an arthroscopic probe according to the invention.
Figure 2:
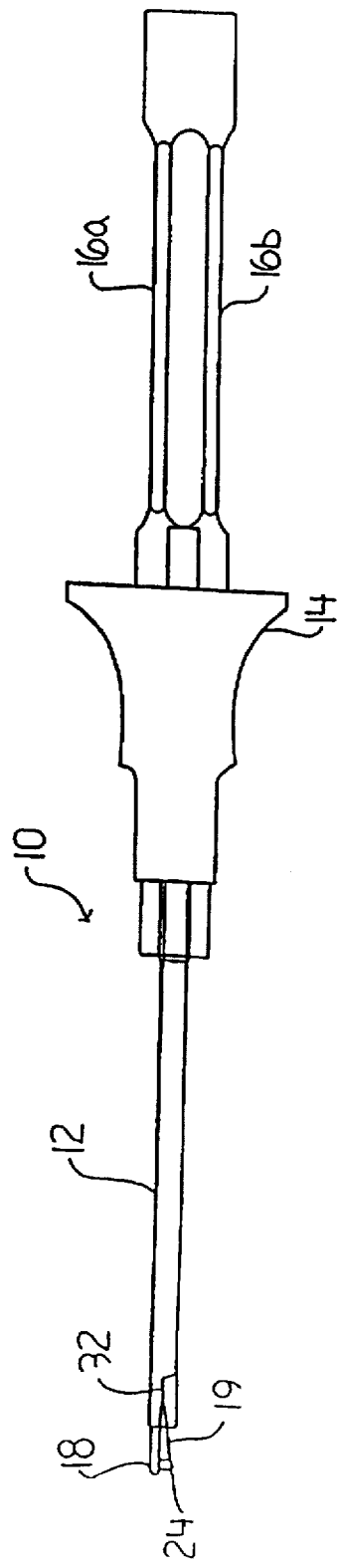
FIG. 2 is a side view of a the arthroscopic probe of FIG. 1 with a modified probe handle.

Referring to FIGS. 1 and 2, there are shown exemplary arthroscopic probes made in accordance with the invention. In FIG. 1, the probe includes a probe body generally designated 10 and made up of an outer cannula 12, flange 14 and handle 16, each for example made of type 316L stainless steel. A stiff shaft 18 and a flexible shaft 19 forming a working end of the probe extend beside each other from a forward end of the handle 16 through the cannula 12. Preferably, the stiff shaft 18 only is attached to the handle 16, while the flexible shaft 19 is attached to the stiff shaft 18 at the working end. The cannula 12 is attached to the flange 14, and the flange 14 is slidably mounted on the handle 16. Pulling back on the handle 16 pulls the cannula 12 back from the working end, exposing the stiff shaft 18 and flexible shaft 19. In this manner the working end of the probe is mounted within the retractable hollow cannula 12. In FIG. 2, the handle 16 is modified slightly to be formed of parallel sections 16a, 16b, and the flange 14 is flared for ease of gripping. Details of the connection of the flange 14 to the handle 16 and shaft 18 are not shown.

The stiff shaft 18 is about 200 mm in total length, with a working end of semi-circular cross-section about 20 mm in length, has an otherwise circular cross-section, with a flat side 22 at the working end of the probe, and terminates in a portion inclined, preferably at right angles, to the shaft thus forming a plunger 24 with a plunger tip 26. The stiff shaft 18 has a diameter of about 4.5 mm, the plunger 24 has a diameter of about 2 mm and both are for example made of A-286 stainless steel. The stiff shaft 18 could be made arcuate, and the plunger portion 24 could be integral with the stiff shaft 18. It is however believed necessary that the terminal portion of the stiff shaft 18 be inclined to the remainder of the shaft 18 so that the plunger tip 26 can be displaced into cartilage without displacing cartilage lying parallel to the stiff shaft further along the stiff shaft 24 towards the handle 16.

This arrangement of the stiff shaft 18 then allows the flexible shaft 19 to flex towards the stiff shaft 18 as the plunger 24 is displaced into cartilage. The flexible shaft 19 terminates in a tip 28 adjacent the plunger tip 26 of the stiff shaft 18. The flexible shaft 19 may be formed as a shim made of flat tempered spring stainless steel. The flexible shaft 19 may be about 15 mm long, 4.5 mm wide and 0.002 mm thick. The flexible shaft 19 is preferably attached to an inclined portion 32 on the flat side 22 of the stiff shaft 18 (see best in FIG. 2). The flexible shaft 19 preferably terminates in prongs 34 that extend on either side of the plunger 24.

Figure 3:
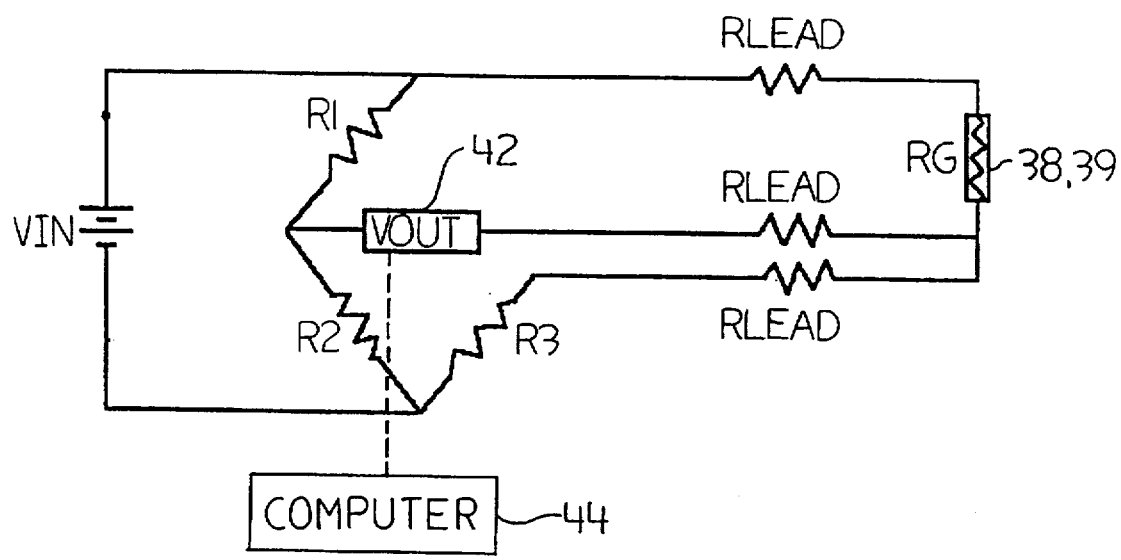
FIG. 3 is an electrical schematic showing a circuit that may be used for the measurement of strain using the device shown in FIGS. 1 and 2.

Identical electric circuits, a schematic of one of which is shown in FIG. 3, are used to sense and record voltage in the strain gauges due to load on the stiff shaft 18 and displacement of the flexible shaft 19 upon displacement of the plunger tip 26 into cartilage. The electric circuit includes a first strain gauge 38 on the stiff shaft 18, which under strain provides a variable resistance, thereby varying voltage appearing at 42 in FIG. 3, the variable voltage thus providing an electrical output corresponding to load in the stiff shaft 18 due to displacement of the plunger tip 26 into cartilage which is indicative of the load on the plunger 24. A second identical electric circuit also includes a second strain gauge 39 on the flexible shaft 19, similarly providing electrical output corresponding to deflection of the flexible shaft 19 due to relative displacement of the plunger tip 26 into cartilage while the flexible shaft 19 rests on relatively undisplaced cartilage in the same area of cartilage. The strain gauges convert load on the stiff shaft (load sensing body) and deflection of the flexible shaft (displacement sensing body) into electrical signals and thereby function as transducers. The displacement of the flexible shaft is relative displacement in relation to the stiff shaft.

The strain gauges 38 and 39 are preferably bonded electrical resistance strain gauges, with gauge factor=2.0, resistance=350Ω and excitation voltage=5 V. The electrical circuits (FIG. 3) each contain a quarter bridge (with $R_1$, $R_2$ and $R_3$ in the bridge) three wire system to compensate for temperature changes in the lead wires, which can have a significant effect on measurements.

The electric output ($V_{out}$ in the exemplary circuit shown) from the two strain gauges is read continuously by a computer 44 as the plunger tip displaces into the cartilage. The output may then be compared with a reference to give absolute values of the stiffness of the cartilage.

In operation, the following steps are carried out: locate tip ends of the stiff shaft and the flexible shaft adjacent cartilage to be tested, preferably with the plunger tip perpendicular to the cartilage surface, continuously measure the strain in each of the stiff shaft and the flexible shaft while displacing a tip end of the stiff shaft into the cartilage which is used to give a continuous output of load and displacement; and compare the measured strain with a reference. The reference may be measured on in vitro samples. For example, a prototype has measured a femoral joint tested on the outside (lateral) half of the joint in three different states of health: normal (fresh), after 12 hours digestion in a degradative enzyme, and after 24 hours digestion. The indentor used as a hand held instrument yielded the following results (N/mm): fresh, 88.0±27.7; 12 hr, 32.3±2.9 and 24 hr, 26.7±5.3. These results compared favourably with measurements using a hydraulic measurement system in a controlled setting.

A person skilled in the art could make immaterial modifications to the invention described and claimed in this patent without departing from the essence of the invention.

The embodiments of the invention in which an exclusive property or privilege is claimed are defined as follows:

1. A tissue softness probe comprising:
   a probe body
   a stiff shaft and a flexible shaft extending beside each other away from the probe body;
   the stiff shaft terminating in an inclined tissue indentation portion having a tissue indentation tip measuring load in a direction parallel to the tissue indentation portion, the flexible shaft terminating in a tip adjacent the tissue indentation tip of the stiff shaft;
   the flexible shaft being oriented to respond to displacement of tissue parallel to the tissue indentation portion; and
   electrical means to sense and record strain in each of the stiff shaft and flexible shaft upon displacement of the tissue indentation tip into tissue.

2. The tissue softness probe of claim 1 in which the tissue indentation portion extends substantially at right angles to the stiff shaft.

3. The tissue softness probe of claim 1 in which the flexible shaft terminates in prongs that extend on either side of the tissue indentation portion.

4. The tissue softness probe of claim 1 in which the electrical means includes:
   a first strain gauge on the stiff shaft having first electrical output corresponding to strain in the stiff shaft due to load on the tissue indentation tip as it is displaced into tissue; and
   a second strain gauge on the flexible shaft having second electrical output corresponding to strain in the flexible shaft due to displacement of the tissue indentation tip into tissue while the flexible shaft rests on relatively undisplaced tissue.

5. The tissue softness probe of claim 4 in which the electrical means includes means to continuously record the first and second electrical output.

6. The tissue softness probe of claim 5 in which the electrical means includes means to compare the recorded first and second electrical output with a reference.

7. The tissue softness probe of claim 1 in which the probe body includes a retractable hollow cannula and the stiff shaft and flexible shaft are mounted within the hollow shaft.

8. The tissue softness probe of claim 1 in which the stiff shaft is semi-circular in cross-section, with a flat side, and the tissue indentation tie extends outward from the flat side.

9. The tissue softness probe of claim 8 in which the flexible shaft is a thin shim attached to the flat side of the stiff shaft.

10. The tissue softness probe of claim 1 in which:
    the probe body includes a retractable hollow cannula and the stiff shaft and flexible shaft are mounted within the hollow shaft;

the stiff shaft is semi-circular in cross-section, with a flat side, at one end of the stiff shaft and the tissue indentation portion extends outward from the flat side substantially at right angles to the stiff shaft;

the flexible shaft is a thin shim attached to the flat side of the stiff shaft and terminates in prongs that extend on either side of the tissue indentation portion; and the electrical means includes:

(a) a first strain gauge on the stiff shaft having first electrical output corresponding to strain in the stiff shaft due to load on the tissue indentation tip as it is displaced into tissue;

(b) a second strain gauge on the flexible shaft having second electrical output corresponding to strain in the flexible shaft due to displacement of the tissue indentation tip into tissue while the flexible shaft rests on relatively undisplaced tissue; and (c) means to continuously record the first and second electrical output and compare the recorded first and second electrical output with a reference.

* * * * *